United States Patent [19]

King et al.

[11] Patent Number: 5,696,129

[45] Date of Patent: Dec. 9, 1997

[54] 5-HT$_4$ ANTAGONISTS

[75] Inventors: Francis David King; Laramie Mary Gaster, both of Bishop's Stortford; Paul Adrian Wyman, Epping; Graham Francis Joiner, Brentwood, all of England

[73] Assignee: SmithKline Beecham p.l.c., Brentford, England

[21] Appl. No.: 406,951

[22] PCT Filed: Sep. 28, 1993

[86] PCT No.: PCT/GB93/02028

§ 371 Date: Mar. 29, 1995

§ 102(e) Date: Mar. 29, 1995

[87] PCT Pub. No.: WO94/07859

PCT Pub. Date: Apr. 14, 1994

[30] Foreign Application Priority Data

| Sep. 29, 1992 | [GB] | United Kingdom | 9220508 |
| Oct. 16, 1992 | [GB] | United Kingdom | 9221774 |
| Oct. 16, 1992 | [GB] | United Kingdom | 9221791 |
| Nov. 5, 1992 | [GB] | United Kingdom | 9223135 |
| Nov. 5, 1992 | [GB] | United Kingdom | 9223138 |
| Nov. 24, 1992 | [GB] | United Kingdom | 9224604 |
| May 11, 1993 | [GB] | United Kingdom | 9309642 |
| Jun. 9, 1993 | [GB] | United Kingdom | 9311878 |

[51] Int. Cl.$^6$ ............ A61K 31/44; C07D 491/147
[52] U.S. Cl. .............. 514/291; 540/481; 540/582; 540/599; 546/89; 514/183; 514/212; 514/214
[58] Field of Search .............. 514/291, 183, 514/212, 214; 546/89; 540/481, 582, 599

[56] References Cited

U.S. PATENT DOCUMENTS 5,189,041  2/1993  Berger ........................... 514/288

5,260,303  11/1993  Becker ........................... 514/300

FOREIGN PATENT DOCUMENTS

| 0 429 984 | 6/1991 | European Pat. Off. . |
| 0 501 322 | 9/1992 | European Pat. Off. . |
| WO 93/02677 | 2/1993 | WIPO . |
| WO 93/05040 | 3/1993 | WIPO . |
| WO 93/08187 | 4/1993 | WIPO . |
| WO 93/16072 | 8/1993 | WIPO . |
| WO93/18036 | 9/1993 | WIPO . |

OTHER PUBLICATIONS

Bockaert, et al, TiPS Reviews, vol. 13, pp. 141–145 (1992).

*Primary Examiner*—C. Warren Ivy
*Assistant Examiner*—Evelyn Huang
*Attorney, Agent, or Firm*—Soma G. Simon; Charles M. Kinzig; Edward T. Lentz

[57] ABSTRACT

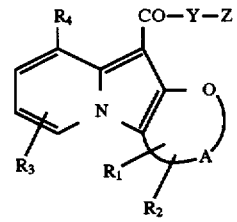

Compounds of formula (I), and pharmaceutically acceptable salts thereof, and the use of a compound of formula (I) or a pharmaceutically acceptable salt thereof in treatment of gastrointestinal disorders, cardiovasular disorders and CNS disorders.

12 Claims, No Drawings

5-HT$_4$ ANTAGONISTS

This application is the national phase of PCT/GB93/02028, filed Sep. 28, 1993.

This invention relates to novel compounds having pharmacological activity, to a process for their preparation and to their use as pharmaceuticals.

EP-A-429984 (Nisshin Flour Milling Co., Ltd.) describes indole derivatives having 5-HT$_3$ receptor antagonist activity. GB 1555682 (Ciba-Geigy) describes a group of 2-methoxy-3-pyridylamides.

European Journal of Pharmacology 146 (1988), 187–188, and Naunyn-Schmiedeberg's Arch. Pharmacol. (1989) 340:403–410, describe a non classical 5-hydroxytryptamine receptor, now designated the 5-HT$_4$ receptor, and that ICS 205-930, which is also a 5-HT$_3$ receptor antagonist, acts as an antagonist at this receptor.

WO 91/16045 (SmithKline and French Laboratories Limited) describes the use of cardiac 5-HT$_4$ receptor antagonists in the treatment of atrial arrhythmias and stroke.

EP-A-501322 (Glaxo Group Limited) describes indole derivatives having 5-HT$_4$ antagonist activity.

WO 93/02677, WO 93/03725, WO 93/05038, WO 93/05040 and PCT/GB93/00506 (SmithKline Beecham plc) describe compounds having 5-HT$_4$ receptor antagonist activity.

It has now been discovered that certain novel compounds also have 5-HT$_4$ receptor antagonist properties.

When used herein, 'treatment' includes prophylaxis as appropriate.

Accordingly, the present invention provides compounds of formula (I), wherein formula (I) consists of formulae (I-1) to (I-8), and pharmaceutically acceptable salts thereof, and the use of a compound of formula (I) or a pharmaceutically acceptable salt thereof:

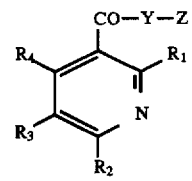

(I-1)

wherein

R$_1$ is C$_{1-6}$ alkoxy;

R$_2$ is hydrogen, C$_{1-6}$ alkyl, amino optionally substituted by a C$_{1-6}$ alkyl group, halo, hydroxy or C$_{1-6}$ alkoxy;

R$_3$ is hydrogen, halo, C$_{1-6}$ alkyl, C$_{1-6}$ alkoxy, nitro, amino or C$_{1-6}$ alkylthio; and R$_4$ is hydrogen, halo, C$_{1-6}$ alkyl, C$_{1-6}$ alkoxy or amino;

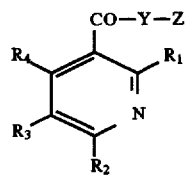

(I-2)

wherein

R$_1$, R$_2$ and R$_3$ are independently hydrogen, halo, C$_{1-6}$ alkyl or C$_{1-6}$ alkoxy;

R$_4$ is hydrogen or C$_{1-6}$ alkyl;

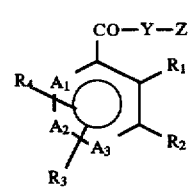

(I-3)

wherein

R$_1$ is O(CH$_2$)$_s$X wherein s is 1 to 3 and X is SOR, COR, CONH$_2$ or OR wherein R is C$_{1-6}$ alkyl;

R$_2$ is hydrogen, C$_{1-6}$ alkyl, amino optionally substituted by a C$_{1-6}$ alkyl group, halo, hydroxy or C$_{1-6}$ alkoxy;

R$_3$ is hydrogen, halo, C$_{1-6}$ alkyl, C$_{1-6}$ alkoxy, nitro, amino or C$_{1-6}$ alkylthio; and R$_4$ is hydrogen, halo, C$_{1-6}$ alkyl, C$_{1-6}$ alkoxy or amino;

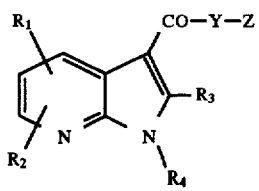

(I-4)

wherein one of A$_1$, A$_2$ and A$_3$ is N and the other two are CH;

R$_1$ and R$_2$ are together either X$_1$-(CH$_2$)$_x$-X$_2$ in which X$_1$-(CH$_2$)$_x$-X$_2$ and the aromatic carbon atoms to which they are attached form a 5–7 membered ring wherein one of X$_1$ and X$_2$ is O, S or CH$_2$ and the other is CH$_2$ and x is 1, 2 or 3;

or R$_1$ and R$_2$ are together X$_3$-CH$_2$—CH=CH—, X$_3$-(CH$_2$)$_2$—CO or X$_3$-(CH$_2$)$_2$—CH(OR$_x$) wherein X$_3$ is O or S and R$_x$ is hydrogen or C$_{1-6}$ alkyl;

and in which an R$_1$/R$_2$ ring may be optionally substituted by one or two C$_{1-6}$ alkyl groups;

R$_3$ and R$_4$ are independently hydrogen, halo, C$_{1-6}$ alkyl or C$_{1-6}$ alkoxy;

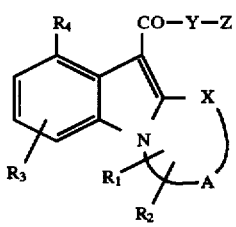

(I-5)

wherein

A is such that N-A-X is N—CO—C$_{1-3}$ [unsaturated or saturated]polymethylene-X where X is O, S, CH$_2$, or NR where R is hydrogen or C$_{1-6}$ alkyl;

R$_1$ and R$_2$ are hydrogen or C$_{1-6}$ alkyl;

R$_3$ is hydrogen, halo, C$_{1-6}$ alkyl, amino, nitro or C$_{1-6}$ alkoxy;

$R_4$ is hydrogen, halo, $C_{1-6}$ alkyl or $C_{1-6}$ alkoxy;

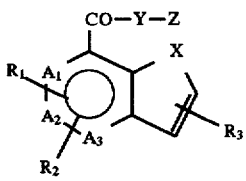
(I-6)

wherein one of $A_1$, $A_2$ and $A_3$ is N and the other two are CH;

X is O or S;

one of $R_1$ and $R_2$ is hydrogen, halo, $C_{1-6}$ alkyl, $C_{1-6}$ alkoxy or amino and the other is hydrogen, halo, $C_{1-6}$ alkyl or $C_{1-6}$ alkoxy;

$R_3$ is hydrogen or $C_{1-6}$ alkyl;

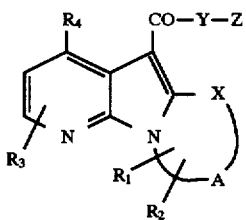
(I-7)

wherein

X is O, S, SO, $SO_2$, $CH_2$, CH, N, or NR wherein R is hydrogen or $C_{1-6}$ alkyl;

A is a saturated or unsaturated polymethylene chain of 2–4 carbon atoms;

$R_1$ and $R_2$ are hydrogen or $C_{1-6}$ alkyl;

$R_3$ is hydrogen, halo, $C_{1-6}$ alkyl, amino, nitro or $C_{1-6}$ alkyl;

$R_4$ is hydrogen, halo, $C_{1-6}$ alkyl or $C_{1-6}$ alkoxy;

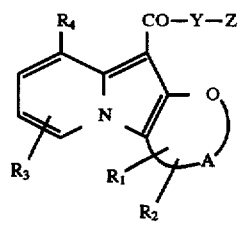
(I-8)

wherein

A is a saturated polymethylene chain of 2–4 carbon atoms;

$R_1$ and $R_2$ are hydrogen or $C_{1-6}$ alkyl;

$R_3$ is hydrogen, halo, $C_{1-6}$ alkyl, amino, nitro or $C_{1-6}$ alkyl;

$R_4$ is hydrogen, halo, $C_{1-6}$ alkyl or $C_{1-6}$ alkoxy;

In formulae (I-1) to (I-8) inclusive:

Y is O or NH;

Z is of sub-formula (a), (b) or (c):

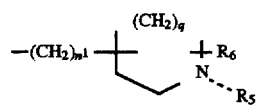
(a)

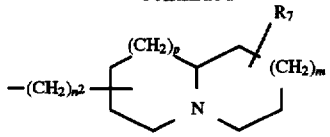
(b)

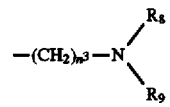
(c)

wherein $n^1$ is 0, 1, 2, 3 or 4; $n^2$ is 0, 1, 2, 3 or 4; $n^3$ is 2, 3, 4 or 5;

q is 0, 1, 2 or 3; p is 0, 1 or 2; m is 0, 1 or 2;

$R_5$ is hydrogen, $C_{1-12}$ alkyl, aralkyl or $R_5$ is $(CH_2)_z$-$R_{10}$ wherein z is 2 or 3 and $R_{10}$ is selected from cyano, hydroxyl, $C_{1-6}$ alkoxy, phenoxy, $C(O)C_{1-6}$ alkyl, $COC_6H_5$, —$CONR_{11}R_{12}$, $NR_{11}COR_{12}$, $SO_2NR_{11}R_{12}$ or $NR_{11}SO_2R_{12}$ wherein $R_{11}$ and $R_{12}$ are hydrogen or $C_{1-6}$ alkyl; and $R_6$, $R_7$ and $R_8$ are independently hydrogen or $C_{1-6}$ alkyl; and $R_9$ is hydrogen or $C_{1-10}$ alkyl;

or a compound of formula (I) wherein the CO-Y linkage is replaced by a heterocyclic bioisostere;

in the manufacture of a medicament having $5\text{-HT}_4$ receptor antagonist activity.

Examples of alkyl or alkyl containing groups include $C_1$, $C_2$, $C_3$, $C_4$, $C_5$, $C_6$, $C_7$, $C_8$, $C_9$, $C_{10}$, $C_{11}$ or $C_{12}$ branched, straight chained or cyclic alkyl, as appropriate. $C_{1-4}$ alkyl groups include methyl, ethyl, n- and iso-propyl, n-, iso-, sec- and tert-butyl. Cyclic alkyl includes cyclopropyl, cyclobutyl, cyclopentyl, cyclohexyl, cycloheptyl and cyclooctyl.

Aryl includes phenyl and naphthyl optionally substituted by one or more substituents selected from halo, $C_{1-6}$ alkyl and $C_{1-6}$ alkoxy.

Halo includes fluoro, chloro, bromo and iodo.

In formula (I-1):

$R_1$ is preferably methoxy.

$R_2$ is preferably amino.

$R_3$ is preferably halo.

$R_3$ is preferably hydrogen.

In formula (I-2):

$R_1$, $R_2$ and $R_3$ are preferably hydrogen.

$R_4$ is often hydrogen.

In formula (I-3):

A particular value for $R_1$ is methoxyethyloxy.

$R_2$ is preferably amino.

$R_3$ is preferably halo such as chloro.

$R_4$ is preferably hydrogen.

In formula (1-4):

$A_1$ may be N, $A_2$ and $A_3$ may be CH.

$R_1$ and $R_2$ may be O—$(CH_2)_3$.

In formula (I-5):

$R_1$, $R_2$ and $R_3$ are preferably hydrogen.

$R_4$ is often hydrogen.

In formula (I-6):

$R_1$ is preferably hydrogen or amino.

$R_2$ is preferably hydrogen or halo.

$R_3$ is preferably hydrogen or halo.

In formula (I-7):

X is often O.

Values for A include —CH$_2$—(CH$_2$)$_r$—CH$_2$— wherein r is 0, 1 or 2; —CH$_2$—CH=CH—; —C(CH$_3$)=CH— or when X is CH or N, A may be —(CH$_2$)$_2$—CH= or —CH=CH—CH=. Other examples of A are as described in the examples hereinafter.

R$_1$ and R$_2$ are often hydrogen or R$_1$ and R$_2$ are gem-dimethyl.

r is often 1.

R$_3$ is preferably hydrogen.

R$_4$ is preferably hydrogen or halo, such as fluoro.

In formula (I-8):

Values for A include —CH$_2$—(CH$_2$)$_r$—CH$_2$— wherein r is 0, 1 or 2.

R$_1$ and R$_2$ are often hydrogen.

r is often 1.

R$_3$ is preferably hydrogen.

R$_4$ is preferably hydrogen or halo, such as fluoro.

A suitable bioisostere for the amide or ester linkage containing Y in formula (I), is of formula (d):

 (d)

wherein the dotted circle represents one or two double bonds in any position in the 5-membered ring; H, J and I independently represent oxygen, sulphur, nitrogen or carbon, provided that at least one of H, J and I is other than carbon; U represents nitrogen or carbon.

Suitable examples of (d) are as described for X, Y and Z in EP-A-328200 (Merck Sharp & Dohme Ltd.), such as an oxadiazole moiety.

Y is preferably O or NH.

When Z is of sub-formula (a), n$^1$ is preferably 2, 3 or 4 when the azacycle is attached at the nitrogen atom and n$^1$ is preferably 1 when the azacycle is attached at a carbon atom, such as the 4-position when q is 2.

When Z is of sub-formula (b), n$^2$ is preferably such that the number of carbon atoms between the ester or amide linkage is from 2 to 4 carbon atoms.

Suitable values for p and m include p=m=1; p=0, m=1, p=1, m=2, p=2, m=1.

When Z is of sub-formula (c), n$^3$ is preferably 2, 3 or 4.

R$_8$ and R$_9$ are preferably both alkyl, especially one of R$_8$ and R$_9$ is C$_4$ or larger alkyl.

Specific values of Z of particular interest are as follows:

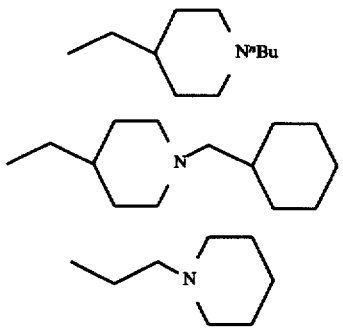

(i)

(ii)

(iii)

-continued

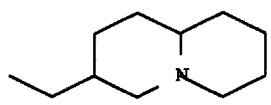 (iv)

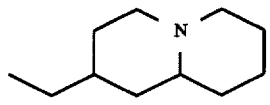 (v)

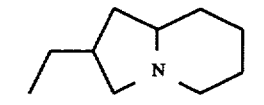 (vi)

(vii)

The invention also provides novel compounds within formula (I) with side chains (i), (ii), (iii), (iv), (v), (vi) or (vii). In a further aspect, the piperidine ring in (i), (ii) or (iii) may be replaced by pyrrolidinyl or azetidinyl, and/or the N-substituent in (9 or (ii) may be replaced by C$_3$ or larger alkyl or optionally substituted benzyl.

In an alternative aspect, the N-substituent in formula (i) or (ii) may be replaced by (CH$_2$)$_n$R$^4$ as defined in formula (I) and in relation to the specific examples of EP-A-501322.

The pharmaceutically acceptable salts of the compounds of the formula (I) include acid addition salts with conventional acids such as hydrochloric, hydrobromic, boric, phosphoric, sulphuric acids and pharmaceutically acceptable organic acids such as acetic, tartaric, maleic, citric, succinic, benzoic, ascorbic, methanesulphonic, α-keto glutaric, α-glycerophosphoric, and glucose-1-phosphoric acids.

Examples of pharmaceutically acceptable salts include quaternary derivatives of the compounds of formula (I) such as the compounds quaternised by compounds R$_x$-T wherein R$_x$ is C$_{1-6}$ alkyl, phenyl-C$_{1-6}$ alkyl or C$_{5-7}$ cycloalkyl, and T is a radical corresponding to an anion of an acid. Suitable examples of R$_x$ include methyl, ethyl and n- and/so-propyl; and benzyl and phenethyl. Suitable examples of T include halide such as chloride, bromide and iodide.

Examples of pharmaceutically acceptable salts also include internal salts such as N-oxides.

The compounds of the formula (I), their pharmaceutically acceptable salts, (including quaternary derivatives and N-oxides) may also form pharmaceutically acceptable solvates, such as hydrates, which are included wherever a compound of formula (I) or a salt thereof is herein referred to.

The compounds of formula (I) wherein CO-Y is an ester or amide linkage are prepared by conventional coupling of the Z moiety with the appropriate acid. Suitable methods are as described in GB 2125398A (Sandoz Limited), GB 1593146A, EP-A-36269, EP-A-289170 and WO 92/05174 (Beecham Group p.l.c.). When CO-Y is replaced by a heterocyclic bioisostere, suitable methods are described in EP-A-328200 (Merck Sharp & Dohme Limited). Reference is also made to EP-A-501322 (Glaxo Group Limited).

The invention also comprises a process for preparing the novel compounds of formula (I) which comprises reacting an appropriate acid derivative with an appropriate alcohol or mine. A process comprises reacting an acid derivative wherein the aromatic substituents are as required in the end compound of formula (I), or substituents convertible thereto, with an alcohol or amine containing Z or a group convertible thereto, and thereafter if necessary, converting the benzoic acid substituents and/or Z, and optionally forming a pharmaceutically acceptable salt.

Suitable examples of conversions in the aromatic substituents include chlorination of hydrogen to chloro, reduction of nitro to amino, dehydrohalogenation such as debromination. Any elaboration is, however, usually carried out prior to ester or amide coupling.

Suitable examples of conversions in the Z containing moiety include conventional modifications of the N-substituent by substitution and/or deprotection or, in the case of a 2-, 3- or 4-substituted piperidinyl desired end compound, reduction of an appropriate pyridyl derivative.

The compounds of the present invention are 5-HT$_4$ receptor antagonists and it is thus believed may generally be used in the treatment or prophylaxis of gastrointestinal disorders, cardiovascular disorders and CNS disorders.

They are of potential interest in the treatment of irritable bowel syndrome (IBS), in particular the diarrhoea aspects of IBS, i.e., these compounds block the ability of 5-HT to stimulate gut motility via activation of enteric neurones. In animal models of IBS, this can be conveniently measured as a reduction of the rate of defaecation. They are also of potential use in the treatment of urinary incontinence which is often associated with IBS.

They may also be of potential use in other gastrointestinal disorders, such as those associated with upper gut motility, and as antiemetics. In particular, they are of potential use in the treatment of the nausea and gastric symptoms of gastro-oesophageal reflux disease and dyspepsia. Antiemetic activity is determined in known animal models of cytotoxic-agent/radiation induced emesis.

Specific cardiac 5-HT$_4$ receptor antagonists which prevent atrial fibrillation and other atrial arrhythmias associated with 5-HT, would also be expected to reduce occurrence of stroke (see A. J. Kaumann 1990, Naumyn-Schmiedeberg's Arch. Pharmacol. 342, 619–622, for appropriate animal test method).

Anxiolytic activity is likely to be effected via the hippocampus (Dumuis et al 1988, Mol Pharmacol., 34, 880–887). Activity can be demonstrated in standard animal models, the social interaction test and the X-maze test.

Migraine sufferers often undergo situations of anxiety and emotional stress that precede the appearance of headache (Sachs, 1985, Migraine, Pan Books, London). It has also been observed that during and within 48 hours of a migraine attack, cyclic AMP levels are considerably increased in the cerebrospinal fluid (Welch et al., 1976, Headache 16, 160–167). It is believed that a migraine, including the prodomal phase and the associated increased levels of cyclic AMP are related to stimulation of 5-HT$_4$ receptors, and hence that administration of a 5-HT$_4$ antagonist is of potential benefit in relieving a migraine attack.

Other CNS disorders of interest include schizophrenia, Parkinson's disease and Huntingdon's chorea.

The invention also provides a pharmaceutical composition comprising a compound of formula (I), or a pharmaceutically acceptable salt thereof, and a pharmaceutically acceptable carrier.

Such compositions are prepared by admixture and are usually adapted for enteral such as oral, nasal or rectal, or parenteral administration, and as such may be in the form of tablets, capsules, oral liquid preparations, powders, granules, lozenges, reconstitutable powders, nasal sprays, suppositories, injectable and infusable solutions or suspensions. Orally administrable compositions are preferred, since they are more convenient for general use.

Tablets and capsules for oral administration are usually presented in a unit dose, and contain conventional excipients such as binding agents, fillers, diluents, tabletting agents, lubricants, disintegrants, colourants, flavourings, and wetting agents. The tablets may be coated according to well known methods in the art, for example with an enteric coating.

Suitable fillers for use include cellulose, mannitol, lactose and other similar agents. Suitable disintegrants include starch, polyvinylpolypyrrolidone and starch derivatives such as sodium starch glycollate. Suitable lubricants include, for example, magnesium stearate.

Suitable pharmaceutically acceptable wetting agents include sodium lauryl sulphate. Oral liquid preparations may be in the form of, for example, aqueous or oily suspensions, solutions, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethylcellulose, aluminium stearate gel or hydrogenated edible fats, emulsifying agents, for example lecithin, sorbitan monooleate, or acacia; non-aqueous vehicles (which may include edible oils), for example, almond oil, fractionated coconut oil, oily esters such as esters of glycerine, propylene glycol, or ethyl alcohol; preservatives, for example methyl or propyl p-hydroxybenzoate or sorbic acid, and if desired conventional flavouring or colouring agents.

Oral liquid preparations are usually in the form of aqueous or oily suspensions, solutions, emulsions, syrups, or elixirs or are presented as a dry product for reconstitution with water or other suitable vehicle before use. Such liquid preparations may contain conventional additives such as suspending agents, emulsifying agents, non-aqueous vehicles (which may include edible oils), preservatives, and flavouring or colouring agents.

The oral compositions may be prepared by conventional methods of blending, filling or tabletting. Repeated blending operations may be used to distribute the active agent throughout those compositions employing large quantities of fillers. Such operations are, of course, conventional in the art.

For parenteral administration, fluid unit dose forms are prepared containing a compound of the present invention and a sterile vehicle. The compound, depending on the vehicle and the concentration, can be either suspended or dissolved. Parenteral solutions are normally prepared by dissolving the compound in a vehicle and filter sterilising before filling into a suitable vial or ampoule and sealing. Advantageously, adjuvants such as a local anaesthetic, preservatives and buffering agents are also dissolved in the vehicle. To enhance the stability, the composition can be frozen after filling into the vial and the water removed under vacuum.

Parenteral suspensions are prepared in substantially the same manner except that the compound is suspended in the vehicle instead of being dissolved and sterilised by exposure of ethylene oxide before suspending in the sterile vehicle. Advantageously, a surfactant or wetting agent is included in the composition to facilitate uniform distribution of the compound of the invention.

The invention further provides a method of treatment or prophylaxis of irritable bowel syndrome, dyspepsia, atrial arrhythmias and stroke, anxiety and/or migraine in mammals, such as humans, which comprises the administration of an effective mount of a compound of the formula (I) or a pharmaceutically acceptable salt thereof.

An amount effective to treat the disorders hereinbefore described depends on the relative efficacies of the compounds of the invention, the nature and severity of the disorder being treated and the weight of the mammal. However, a unit dose for a 70 kg adult will normally contain 0.05 to 1000 mg for example 0.5 to 500 mg, of the compound of the invention. Unit doses may be administered once or more than once a day, for example, 2, 3 or 4 times a day, more usually 1 to 3 times a day, that is in the range of approximately 0.0001 to 50 mg/kg/day, more usually 0.0002 to 25 mg/kg/day.

No adverse toxicological effects are indicated within the aforementioned dosage ranges.

The invention also provides a compound of formula (I) or a pharmaceutically acceptable salt thereof for use as an active therapeutic substance, in particular for use in the treatment of irritable bowel syndrome, gastro-oesophageal reflux disease, dyspepsia, atrial arrhythmias and stroke, anxiety and/or migraine.

The following Examples illustrates the preparation of compounds of formula (I), and the following Descriptions relate to the preparation of intermediates. The compounds of formula (I-1) and intermediates are prepared in Examples and Descriptions 1-1, 2-1 etc, the compounds of formula (I-2) are prepared in Examples and Descriptions 1-2, 2-2 etc and similarly for the compounds of formulae (I-3) to (I-8).

It will be appreciated that any compound prepared wherein Y is O may be provided as the corresponding compound wherein Y is NH.

DESCRIPTION 1-1

6-Amino-5-chloro-2-methoxypyridine-3-carboxylic Acid a) A solution of 12 g of 2,6-difluoropyridine in 40 ml of iso-propanol was heated to 140° C. with 20 ml of aqueous ammonia (d=0.88) for 3 h in a sealed bomb. The cooled reaction was concentrated by rotary evaporation, the product extracted into ethyl acetate (100 ml) and the solution washed with aqueous $Na_2CO_3$ and dried ($K_2CO_3$). Evaporation afforded 2-amino-6-fluoropyridine (7.1 g).

$^1$H-NMR (CDCl$_3$)

δ:4.59 (s, 2H) 6.20 (dd, 1H) 6.31 (dd, 1H) 7.50 (q, 1H)

b) A solution of 2-amino-6-fluoropyridine (4.2 g) in $CH_2C_2$ (100 ml) was treated with Et$_3$N (8 ml) and pivaloyl chloride (5 ml) at 0° C. to room temperature overnight. The reaction mixture was washed with water (50 ml), 2N $H_2SO_4$ (50 ml), water (50 ml) and dried (Na$_2$SO$_4$). Evaporation of the solvent afforded 6-fluoro-2-pivaloylaminopyridine (6 g).

$^1$H-NMR (CDCl$_3$)

δ:1.33 (s, 9H) 6.65 (dd, 1H) 7.79 (q, 1H)7.90 (brs, 1H) 8.11 (dd, 1H)

c) A solution of 6-fluoro-2-pivaloylaminopyridine (2 g) in THF (30 ml) was cooled to −78° C. and BuLi (15 mL of 1.6M in hexane) was added and the reaction stirred at 0° C. for 2 h. On re-cooling to −78° C., ethyl chloroformate (2 mL) was added and the reaction allowed to warm slowly to room temperature over 1 h. Water (10 ml) was added and the products extracted into Et$_2$O (3×50 ml) and dried (Na$_2$SO$_4$). Concentration afforded an oil which was triturated with petrol to give a solid, the isomeric 2-pivaloylamino-6-fluoropyridine-3-carboxylate ($^1$H NMR [CDCl$_3$] δ1.36 (s, 9H), 1.43 (t, 3H), 4.41 (q, 2H), 6.64 (dd, 1H), 8.45 (t, 1H), 11.34 (brs, 1H). The mother liquors were concentrated and purified by flash column chromatography (SiO$_2$, Petrol to 5% Et$_2$O/petrol to give ethyl 2-fluoro-6-pivaloylaminopyridine-3-carboxylate (1.2 g).

$^1$H-NMR (CDCl$_3$)

δ:1.33 (s, 9H) 1.41 (t, 3H) 4.40 (q, 2H) 8.07 (brs, 1H) 8.20 (dd, 1H) 8.40 (t, 1H)

d) A solution of methyl-6-pivaloylamino-2-fluoropyridine-3-carboxylate (2.1 g) in MeOH (100 ml) was heated under reflux with KOBu-t (2.6 g) for 2 h. The solvent was evaporated and aqueous NaHCO$_3$ (50 mL) added. The solid product, methyl-6-amino-2-methoxypyridine-3-carboxylate was collected and dried (1.4 g).

$^1$H-NMR (CDCl$_3$)

δ:3.82 (s, 3H) 3.96 (s, 3H) 4.78 (brs, 2H) 6.06 (d, 1H) 8.01 (d, 1H)

e) A solution of methyl-6-amino-2-methoxypyridine-3-carboxylate (0.4 g) in acetic acid (10 ml) was treated with a solution of Cl$_2$ (0.19 g) in HOAc (4 ml) at room temperature for 3 h. The AcOH was removed by rotary evaporation and the residue treated with aqueous NaHCO$_3$ (50 mL) and the product extracted into EtOAc (100 mL). Evaporation afforded methyl-6-amino-5-chloro-2-methoxypyridine-3-carboxylate (0.32 g).

$^1$H-NMR (CDCl$_3$)

δ:3.81 (s, 3H) 3.94 (s, 3H) 5.26 (brs, 2H) 8.05 (s, 1H)

f) A solution of methyl-6-amino-5-chloro-2-methoxypyridine-3-carboxylate (0.32 g) in MeOH (5 mL) was treated with 2.5N NaOH (0.6 mL) and H$_2$O (5 mL) and the reaction stirred at room temperature until the reaction was complete by TLC. The MeOH was removed by rotary evaporation and the residue carefully acidified with 5N HCl to give the title compound which was collected and dried (0.15 g).

$^1$H-NMR (d$^6$-DMSO)

δ:3.82 (s, 3H) 7.08 (brs, 2H) 7.88 (s, 1H) 12.10 (brs, 1H)

DESCRIPTION 2-1

6-Amino-5-chloro-2-ethoxypyridine-3-carboxylic acid a) A stirred solution of diisopropylamine (9.8 ml) in dry THF (100 ml) was cooled to −60° C. and a solution of MeLi (LiBr complex, 1.5M in Et$_2$O, 45 ml) was added over 1 minute and the reaction stirred at 0° C. for 10 minutes. The reaction was re-cooled to −60° C. and 2,6-difluoropyridine (6.5 ml) was added in one portion and the reaction stirred below −60° C. for 1 hour after which time a precipitate had formed. The mixture was then cooled with liquid nitrogen to −80° C. and a solution of di-t-butyl dicarbonate (15 g) in dry Et$_2$O (10 ml) was added as quickly as possible keeping the internal temperature below −80° C. After addition was complete the reaction was stirred below −70° C. for 0.5 hour by which time all the solid had dissolved. The mixture was poured onto ice/water and the product extracted into 1:1 petrol/ether (300 ml). The organic extracts were washed with 1M NaOH, water, 1M H$_2$SO$_4$ (100 ml of each) and dried (MgSO$_4$). The solution was filtered through a bed of silica (ca. 50 ml) to remove red, base-line material. The silica was washed with a further quantity (500 ml) of 1:1 petrol/ether to collect all of the product. Rotary evaporation of the combined extracts afforded 12.7 g of crude material used without further purification.

The crude material was dissolved in EtOH (200 ml) and 0.88 ammonia (50 ml) was added. After standing at room temperature overnight, the reaction mixture was evaproated to dryness, the residue treated with water (100 ml) and the product extracted into CHCl$_3$ (2×200 ml) and dried (MgSO$_4$). The extracts were filtered through silica (100 ml), first eluting with CHCl$_3$ to collect the 2-amino isomer, then with 3:2 CHCl₃: EtOAc to collect tert-butyl 6-amino-2-fluoropyridine-3-carboxylate (4.6 g, 30%).

¹H NMR (CDCl₃) 250 MHz

δ: 8.0 (t, 1H), 6.32 (d, 1H), 5.59 (br s, 2H), 1.59 (s, 9H)

b) tert-Butyl 6-amino-2-fluoropyridine-3-carboxylate (0.7 g, 0.0033 mol) in EtOH (25 ml) was treated with potassium tert-butoxide (0.39 g, 0.0035mol) and the mixture was heated under reflux overnight. After cooling to room temperature, saturated NaHCO₃ solution was added and the precipitated solid was collected by filtration and dried/n vacuo to give tert-butyl 6-amino-2-ethoxypyridine-3-carboxylate(0.6 g).

¹H NMR (d⁶DMSO) 250 MHz

δ: 7.72 (d, 1H), 6.61 (s, 2H), 5.99.(d, 1H), 4.24 (q, 2H), 1.47 (s, 9H), 1.29 (t, 3H)

c) tert-Butyl 6-amino-2-ethoxypyridine-3-carboxylate (0.6 g, 0.0027 mol) was dissolved in glacial AcOH (10 ml) and a solution of chlorine in AcOH (4 ml of a solution of 5.3 g Cl₂ in 100 ml AcOH, 0.003mol) was added and the reaction mixture stirred at room temperature overnight.

The solvent was removed in vacuo, the residue dissolved in CHCl₃, washed with saturated NaHCO₃ solution, dried (MgSO₄) and evaporated in vacuo to leave a dark oil (0.33 g).

The oil was dissolved in trifluoroacetic acid (20 ml) and the solution stirred at room temperature for 3 hours.

The solvent was removed in vacuo and the residue was dissolved in CHCl₃, washed twice with saturated NaHCO₃ solution, dried (MgSO₄) and evaporated to dryness. The title compound was isolated as a pale oil (0.2 g).

¹H NMR (CDCl₃) 250 MHz

δ: 8.21 (s, 1H), 7.27 (s, 1H), 5.40–5.24 (br s, 2H), 4.55 (q, 2H), 1.48 (t, 3H).

DESCRIPTION 3-1

6-Amino-5-chloro-2-propoxypyridine-3-carboxylic acid

The following intermediate was prepared analagously to the method of Description 2-1 above ¹H NMR (CDCl₃) 250 MHz δ: 8.22 (s, 1H), 7.28 (s, 1H), 5.49–5.20 (br s, 2H), 4.45 (t, 2H), 1.92–1.66 (m, 2H), 1.02 (t, 3H)

EXAMPLE 1-1

[R₁=CH₃O, R₂=NH₂, R₃=Cl, R₄=H, Y=O, Z=(iii)]

1-Piperidinylethyl-6-amino-5-chloro-2-methoxypyridine-3-carboxylate

A suspension of 6-amino-5-chloro-2-methoxypyridine-3 carboxylic acid (0.1 g) and biscarbonyldiimidazole (0.08 g) in CH₃CN (5 ml) was heated to 40° C. for 1 h to give a solution. The reaction mixture was evaporated to dryness and the residue re-dissolved in dry THF (10 ml). This was added to a stirred solution of the lithium salt of (2-hydroxyethyl)piperidine (prepared from 0.09 g of alcohol and 0.43 mL of 1.6M n-BuLi) in dry THF (10 ml) at 0° C. After stirring at room temperature for 3 h, the solvent was removed by rotary evaporation, the residue treated with an excess of cold 0.5N NaOH solution and the product extracted into EtOAc (3×50 ml). The dried (K₂CO₃) extracts were filtered, concentrated and the residue recrystallised from EtOAc/petrol to give the title compound (77 mg).

mp 122°–124° C.

NMR (CDCl₃) 250 MHz

δ: 8.04(s, 1H), 5.22(brs, 2H), 4.39(t,2H), 3.94(s,3H), 2.71(t,2H), 2.55–2.43(m,4H), 1.58–1.52(m,4H), 1.50–1.47 (m,2H)

EXAMPLE 2-1

[R₁=CH₃O, R₂=NH₂, R₃=Cl, R₄=H, Y=O, Z=(i)]

(1-Butyl-4-piperidinyl)methyl 6-amino-5-chloro-2-methoxypyridine-3-carboxylate oxalate The title compound was prepared in an analogous manner to Example 1-1.

mp 193°–194° C.,

NMR (d⁶-DMSO) 250 MHz

δ: 7.92(s,1H), 6.47(brs, 2H), 4.10(d,2H), 3.91(s,3H), 3.62–3.48(m,2H), 3.05–2.74(m,4H), 2.15–1.60(m,7H), 1.35 (sex, 2H), 0.95(t,3H)

EXAMPLE 3-1

[R₁=C₂H₅O, R₂=NH₂, R₃=Cl, R₄=H, Y=O, Z=(i)]

(1-Butyl-4-piperidinyl)methyl 6-amino-5-chloro-2-ethoxypyridine-3-carboxylate oxalate salt A solution of 6-amino-5-chloro-2-ethoxypyridine-3-carboxylic acid (0.2 g, 0.001 mol) in MeCN (10 ml) was treated with 1,1-carbonyldiimidazole (0.16 g, 0.001 mol) and the resulting solution was stirred at room temperature for 2 hours after which time the solvent was removed in vacuo.

1-Butyl-4-piperidinemethanol (0.17 g, 0.001mol) was dissolved in dry THF (10 ml) and 1.5M methyllithium (0.66ml, 0.001mol) was added dropwise. The mixture was stirred at room temperature for 10 minutes. The imidazolide was dissolved in dry THF (10 ml) and the solution added dropwise. The mixture was stirred at room temperature for 65 hours. Water was added and the solvent removed in vacuo. The residue was dissolved in CHCl₃, washed with water, dried (MgSO₄) and evaporated in vacuo to give a pale oil. This was purified by column chromatography on SiO₂ eluting with CHCl₃ EtOH to give the title compound as a pale oil (0.043 g) which was converted to the oxalate salt.

¹H NMR (d⁶DMSO) 250 MHz

δ: 7.87 (s, 1H), 7.12 (br s, 2H), 4.30 (q, 2H), 4.01 (d, 2H), 3.52–3.30 (br d, 2H), 3.06–2.72 (m, 4H), 2.00–1.80 (br d, 2H), 1.71–1.42 (m, 4H), 1.37–1.19 (m, 5H), 0.90 (t, 3H).

EXAMPLE 4-1

[R₁=C₃H₇O, R₂=NH₂, R₃=Cl, R₄=H, Y=O, Z=(i)]

(1-Butyl-4-piperidinyl)methyl 6-amino-5-chloro-2-propoxypyridine-3-carboxylate oxalate salt The title compound was prepared in an analogous manner to Example 3-1.

¹H NMR (d⁶DMSO) 250 MHz

δ: 7.88 (s, 1H), 7.15 (s, 2H), 4.19 (t, 2H), 4.09–3.95 (m, 2H), 3.50–3.33 (m, 2H), 3.03–2.75 (m, 4H), 2.04–1.40 (m, 9H), 1.38–1.20 (m, 2H), 0.96 (t, 3H), 0.90 (t, 3H).

DESCRIPTION 1-2

7-Azaindole-3-carboxylic acid

Following the procedure outlined by M. M. Robinson and B. L. Robinson, JACS 78 (1956), 1247, 7-Azaindole-3- carboxaldehyde (M. M. Robinson & B. L. Robinson, JACS 77 (1955), 457) (1.0 g, 6.84mmol) was converted to the title compound (358 mg, 32%).

$^1$H NMR (250 MHz, CD$_3$SOCD$_3$)

δ 12.4 (brs, 1H), 12.23 (brs, 1H), 8.4–8.2 (m, 2H), 8.13 (s, 1H), 7.28–7.15 (m, 1H)

EXAMPLE 1-2

[R$_1$,R$_2$,R$_3$,R$_4$=H, Y=O, Z=(i)]

(1-Butyl-4-piperidinyl)methyl-7-azaindole-3-carboxylate

7-Azaindole-3-carboxylic acid (100 mg, 0.617mmol) was stirred in thionyl chloride (8 ml) under nitrogen for 4 h. The solvent was removed in vacuo to afford crude acid chloride.

Methyl lithium (1.5M in diethylether, 0.4 ml) was added dropwise to a cooled (0° C.) solution of 1-butyl-4-piperidine-methanol (0.110 g, 0.643 mmol) in dry THF (5 ml) under nitrogen atmosphere. Stirring was continued for 10 minutes. A solution of the acid chloride in dry THF (10 ml) was added and stirring continued overnight. Water was added and the solvent concentrated in vacuo. The residue was partitioned between chloroform and water. The organic phase was dried (Na$_2$SO$_4$) filtered and concentrated. the residue was chromatographed on silica using chloroform and methanol as eluant to afford the title compound as a yellow solid (69 mg, 35%)

$^1$H NMR (250 MHz, CDCl$_3$)

δ 12.09 (brs, 1H), 8.48 (d, 1H), 8.42 (d, 1H), 8.15 (s, 1H), 7.35–7.2 (m, 1H), 4.25 (d, 2H), 3.08 (d, 2H), 2.40 (t, 2H),2.05 (t, 2H), 1.95–1.77 (m, 3H), 1.6–1.2 (m, 6H), 0.94 (t, 3H)

DESCRIPTION 1-3

6-Amino-5-chloro-2-(2-methoxyethoxy)pyridine-3-carboxylic acid

This compound was prepared in an analogous manner to the compound of Description 2-1.

$^1$H NMR (d$^6$DMSO) 250 MHz

δ: 7.85 (s, 1H), 7.05 (br s, 2H), 4.35 (t, 2H), 3.64 (t, 2H), 3.3 (s, 3H)

EXAMPLE 1-3

[R$_1$=CH$_3$OC$_2$H$_5$O, R$_2$=NH$_2$, R$_3$=Cl, R$_4$=H, Y=O, Z=(i)]

(1-Butyl-4-piperidinyl)methyl 6-amino-5-chloro-2-(2-methoxyethoxy)pyridine-3-carboxylate The title compound was prepared in an analogous manner to that described in Example 3-1.

$^1$H NMR (free base) (CDCl$_3$) 250 MHz

δ: 8.05 (s, 1H), 5.14 (s, 2H), 4.45 (t, 2H), 4.10 (d, 2H), 3.75 (t, 2H), 3.45 (s, 3H), 3.12–2.95 (m, 2H), 2.49–2.32 (m, 2H), 2.11–1.95 (m, 2H), 1.9–1.7 (m, 3H), 1.62–1.2 (m, 6H), 0.92 (t, 3H).

EXAMPLE 1-4

[A$_1$=N, A$_2$,A$_3$=CH; R$_1$,R$_2$=O—(CH$_2$)$_3$, R$_3$,R$_4$Y=O, Z=(i)]

(1-Butyl-4-piperidinyl)methyl-2H-3,4-dihydropyrano[2,3-c]pyridine-8-carboxylate

The title compound is prepared from 2H-3,4-dihydropyrano[2,3-c]pyridine-5-carboxylic acid and lithium (1-butylpiperidin-4-yl) methoxide via the imidazolide.

EXAMPLE 2-4

[A$_2$=N, A$_1$,A$_3$=CH; R$_1$,R$_2$=O(CH$_2$)$_3$, R$_3$,R$_4$=Y=O, Z=(i)]

(1-Butyl-4-piperidinyl)methyl-2H-3,4-dihydropyrano[3,2-c]pyridine-8-carboxylate

The title compound is prepared from 2H-3,4-dihydropyrano[3,2-c]pyridine-8-carboxylic acid and lithium (1-butylpiperidin-4-yl) methoxide via the imidazolide.

EXAMPLE 3-4

[A$_3$=N, A$_1$,A$_2$=CH; R$_1$,R$_2$=O—(CH$_2$)$_3$, R$_3$,R$_4$Y=O, Z=(i)]

(1-Butyl-4-piperidinyl)methyl -2H-3,4-dihydropyrano[3,2-b]pyridine-5-carboxylate The title compound is prepared from 2H-3,4-dihydropyrano[3,2-b]pyridine-5-carboxylic acid and lithium (1-butylpiperidin-4-yl) methoxide via the imidazolide.

EXAMPLE 1-5

[X=O, A=CO—(CH$_2$)$_2$—, R$_1$–R$_4$=H, Y=O, Z=(i)]

10-(1-Butyl-4-piperidinyl)methyl 2,3-dihydro-4-oxo-4H-[1,3]oxazino[3,2-a]indolecarboxylate The title compound is prepared from 2,3-dihydro-4-oxo-4H-[1,3]oxazinoindole[3,2-a]indole-10-carboxylic acid by reaction of lithium (1-butylpiperidin-4-yl)methoxide via the imidazolide.

EXAMPLE 2-5

[X=NH, A=CO—CH=C(CH$_3$)—, R$_1$–R$_4$=H, Y=O, Z=(i)]

(1-Butyl-4-piperidinyl)methyl-2-methyl-1H-4-oxo-4H-pyrimido[1,2-a]indole-10-carboxylate The title compound is prepared from methyl 2-methyl-1H-4-oxo-4H-pyrimido[1,2-a]indole-10-carboxylate (Ian T. Forbes et al., J. Chem. Soc. Perkin Trans. 1 (1992) 275–281) according to the method described in Example 1–8.

DESCRIPTION 1-6

2-Methylfurano[2,3-c]pyridine-7-carboxylic acid a) A solution of 2-bromo-3-hydroxypyridine (10 g) in dry THF (100 ml) was treated with 1 equivalent of sodium hydride (80% in oil) (1.72 g) and stirred at room temperature under nitrogen for 0.75 hours. Propargyl bromide (80% in toluene) (19.2 ml) was added and the mixture was heated under reflux for 88 hours. After cooling, the solvent was evaporated under reduced pressure and the residue partitioned between 5% aqueous NaOH and EtOAc. The organic layer was removed, dried (Na$_2$SO$_4$) and concentrated in vacuo to give a pale yellow gum. This was purified by column chromatography on silica using dichloromethane as eluant to give 2-bromo-3-propargyloxypyridine as an off white solid 6 g.

$^1$H NMR 250 MHz (CDCl$_3$)

δ: 8.05 (d, 1H), 7.35 (d,1H), 7.3–7.2 (m, 1H), 4.81 (d,2H), 2.59 (t, 1H).

b) 2-Bromo-3-propargyloxypyridine (9.4 g) was heated under reflux under nitrogen in dichloromethane (100 ml) for 64 hours, then the solvent was removed in vacuo and the residue purified by column chromatography on silica using dichloromethane as eluant to give 7-bromo-2-methylfurano [2,3-c]pyridine as a tan solid (4.3 g, 46%).

$^1$H NMR 250MHz (CDCl$_3$)

δ: 8.12 (d, 1H), 7.39 (d,1H), 6.50 (s, 1H), 2.56 (s,3H).

c) A solution of 7-bromo-2-methylfurano[2,3-c]pyridine (1.76 g) in dry diethyl ether (45 ml) under an atmosphere of nitrogen, was cooled to −78° C. and treated with n-butyllithium (1.6M in hexane) (5.8 ml). After stirring for 2 hours, the reaction mixture was poured onto a mixture of solid carbon dioxide pellets and diethyl ether (5 ml). After warming to room temperature, the solvent was removed under reduced pressure. The residue was triturated with diethyl ether and filtered to give the title compound as a pale pink powder 1.45 g.

$^1$H NMR 250MHz (DMSO)

δ: 8.15 (d, 1H), 7.60 (d,1H), 6.70 (s,1H), 2.51 (s,3H).

EXAMPLE 1-6

[A$_1$=N, A$_2$/A$_3$=CH, X=O; R$_1$/R$_2$=H, R$_3$=2—CH$_3$, Y+Z=(i)]

(1-Butyl-4-piperidinyl)methyl-2-methylfurano[2,3-c] pyridine-7-carboxylate hydrochloride A solution of 2-methylfurano[2,3-c]pyridine-7-carboxylic acid (400 mg) in dry dichloromethane (12 ml) was treated with oxalyl chloride (0.32 ml) and 2 drops of DMF. The mixture was stirred at room temperature for 2 hours then the solvent was removed in vacuo and the residue dried under vacuum to afford the crude acid chloride.

Methyllithium (1.5M in diethyl ether, 1.66 ml) was added dropwise to a cooled solution of 1-butyl-4-piperidinemethanol (386 mg) in dry THF(10 ml). Stirring was continued for 10 mins. A solution of the acid chloride from above in dry THF (20 ml) was added and the reaction mixture was stirred at room temperature overnight. The solvent was removed in vacuo and the residue partitioned between water and dichloromethane. The organic layer was removed and the residue purified by column chromatography on silica to give a colourless gum. This was converted to the hydrochloride salt 84 mg mp 178°–180° C.

$^1$H NMR 200 MHz (CDCl$_3$) (free base)

δ: 8.5 (d,1H), 7.61(d, 1H), 6.5 (s, 1H), 4.38 (d,2H), 3.0 (d,2H), 2.6 (s,3H), 2.42–2.28 (m,2H), 2.1–1.8 (m, 5H), 1.65–1.15 (m,6H), 0.92 (t,3H).

DESCRIPTION 1-7

7-Azaindole-3-carboxylic acid

Following the procedure outlined by M. M. Robinson and B. L. Robinson, JACS 78 (1956), 1247, 7-Azaindole-3-carboxaldehyde (M. M. Robinson & B. L. Robinson, JACS 77 (1955), 457) (1.0 g, 6.84 mmol) was converted to the title compound (358 mg, 32%).

$^1$H NMR (250 MHz, CD$_3$SOCD$_3$)

δ12.4 (brs, 1H), 12.23 (brs, 1H), 8.4–8.2 (m, 2H), 8.13 (s, 1H), 728–7.15 (m, 1H)

EXAMPLE 1-7

[X=O, A=(CH$_2$)$_3$, R$_1$,R$_2$,R$_3$,R$_4$, =H, Y=O, Z=(i)]

(1-Butyl-4-piperidinyl)methyl 3,4-dihydro-2H-pyrido[2'3':6,7]pyrrolo[2,1-b]oxazine-10-carboxylate hydrochloride a) 7-Azaindole-3-carboxylic acid (100 mg, 0.617 mmol) was stirred in thionyl chloride (8 ml) under nitrogen for 4 h. The solvent was removed in vacuo to afford crude acid chloride.

Methyl lithium (1.5M in diethylether, 0.4 ml) was added dropwise to a cooled (0° C.) solution of 1-butyl-4-piperidine-methanol (0.110 g, 0.643 mmol) in dry THF (5 ml) under nitrogen atmosphere. Stirring was continued for 10 minutes. A solution of the acid chloride in dry THF (10 ml) was added and stirring continued overnight. Water was added and the solvent concentrated in vacuo. The residue was partitioned between chloroform and water. The organic phase was dried (Na$_2$SO$_4$) filtered and concentrated. The residue was chromatographed on silica using chloroform and methanol as eluant to afford (1-butyl-4-piperidinylmethyl 7-azaindole-3-carboxylate as a yellow solid (69 mg, 35%)

$^1$H NMR (250 MHz, CDCl$_{13}$)

δ12.09 (brs, 1H), 8.48 (d, 1H), 8.42 (d, 1H), 8.15 (s, 1H), 7.35–7.2 (m, 1H), 4.25 (d, 2H), 3.08 (d, 2H), 2.40 (t, 2H),2.05 (t, 2H), 1.95–1.77 (m, 3H), 1.6–1.2 (m, 6H), 0.94 (t, 3H)

b) To a stirred suspension of (1-Butyl-4-piperidinylmethyl 7-azaindole-3-carboxylate (213 mg,0.67 mmol) in CHCl$_3$ (10 ml) under an atmosphere of nitrogen, was added 3-bromopropanol (0.12 ml, 1.3 mmol) and this mixture was treated portionwise over 5 minutes with N-chlorosuccinimide (99 mg, 0.74 mmol). After 2.5 hours, ethereal HCl (1M, 0.07 ml,0.07 mmol) was added and stirring was continued overnight, then the reaction mixture was basified with 10% Na$_2$CO$_3$ solution and extracted with CHCl$_3$. The extract was dried and concentrated to leave a brown gum, which was dissolved in acetone (10 ml), treated with anhydrous K$_2$CO$_3$, (200 mg, 1.4 mmol) and stirred at room temperature for 18 hours. The mixture was evaporated IN vacuo to give an oil which was purified by column chromatography on silica using CHCl$_3$/MeOH as eluant. The product was converted to the hydrochloride salt 13 mg, mp 168°–170° C.

$^1$H NMR 250 MHz (CDCl$_3$) (free base)

δ:8.22–8.1 (m,2H), 7.2–7.12 (m,1H), 4.61 (t,2H), 4.38–4.15(m, 4H), 3.25–3.0 (m,2H), 2.6–1.1 (m, 15H), 0.92 (t,3H)

DESCRIPTION 1-8

Ethyl 3,4-dihydro-2H-pyrano[2,3-b]indolizine-10-carboxylate a) A mixture of ethyl 2-pyridylacetate (6.0 g, 0.036 mole) and ethyl bromoacetate (4.4 ml, 0.038 mole) was allowed to stand at room temperature for 72 h, during which time the product gradually crystallised out. The mixture was treated with acetone (80 ml) to dissolve unreacted starting materials and then filtered. The solid collected was dried under vacuum to afford 1,2-di-[(ethoxycarbonyl)methyl] pyridinium bromide as a beige solid (3.53 g, 30%).

$^1$H NMR (CDCl$_3$)

δ:9.77(d, 1H), 8.61 (dd, 1H), 8.27 (d, 1H), 8.08 (dd, 1H), 6.13 (s,2H), 4.50(s,2H), 4.30(q,2H), 4.21(q,2H), 1.33(t,3H), 1.28(t,3H).

b) A solution of 1,2-di-[(ethoxycarbonyl)methyl] pyridinium bromide (1.5 g, 0.0045 mole) and 1,3-dibromopropane (0.45 ml, 0.0045 mole) in ethanol (10 ml) was added over 5 minutes to a stirred solution of potassium hydroxide (0.75 g, 0.0134 mole) in ethanol (15 ml) at 5° C. The mixture was then allowed to warm upto room temperature and stir for 20 h. The reaction mixture was diluted with water (150 ml) and extracted with ethyl acetate (2×100 ml). The combined extracts were dried (Na$_2$SO$_4$) and concentrated in vacuo to leave a brown oil. This was chromatographed on silica gel eluting with ether to afford the title compound as a yellow oil.

$^1$H NMR (CDCl$_3$)

δ: 8.11 (d, 1H), 7.66(d,1H), 7.03(dd,1H), 6.74(dd,1H), 4.39(q,2H), 4.33(t,2H), 2.76(t,2H), 2.10–2.25(m,2H), 1.42 (t,3H).

DESCRIPTION 2-8

(1-Butyl-4-piperidinyl)methanol

A mixture of ethyl isonipecotate (102 g, 0.65 mole) and 1-bromobutane (72 ml, 0.67 mole) in ethanol (1.2 L) was treated with anhydrous potassium carbonate (180 g, 1.3 mole) and heated under reflux for 2 h. The mixture was allowed to cool an then filtered through kieselguhr. The filtrate was concentrated in vacuo to leave a yellow oil, which was dissolved in ether (300 ml) and added dropwise over 20 minutes to a stirred suspension of lithium aluminium hydride (50 g, 1.3 mole) in ether (500 ml) at 0° C. under nitrogen. The mixture was stirred at room temperature for 18 h, then cooled to 0° C. and treated with water (50 ml), 10% NaOH solution (50 ml) and water (150 ml). The mixture was filtered through keiselguhr and the filtrate concentrated under vacuum to leave a pale yellow oil, which was distilled to afford the title compound as a colourless oil (88.5 g, 80%) bp 102°–108° C. at 0.1 mm Hg.

$^1$H NMR (CDCl$_3$)

δ: 3.48(d,2H), 2.88–3.03(m,2H), 2.25–2.38(m,2H), 2.10 (br s, 1H), 1.66–2.00(m,4H), 1.17–1.60(m,7H), 0.90(t,3H).

EXAMPLE 1-8

[A$_1$=N, A$_2$,A$_3$=CH, X=O; R$_1$,R$_2$,R$_3$=H, Y=O, Z=(i)]

(1-Butyl-4-piperidinyl)methyl 3,4-dihydro-2H-pyrano[2,3-b]indolizine-10-carboxylate A stirred solution of (1-butyl-4-piperidinyl)methanol (125 mg, 0.72 mmole) in dry THF (5 ml) at 5° C. under argon was treated with 1.5M methyllithium in ether (0.35 ml, 0.50 mmole). After 10 minutes, a solution of ethyl 3,4-dihydro-2H-pyrano[2,3-b]indolizine-10-carboxylate (55 mg, 0.22 mmole) in dry THF (5 ml) was added and the mixture heated under reflux for 3 h. The mixture was then allowed to cool and concentrated in vacuo. The residue was treated with 10% Na$_2$CO$_3$ solution (10 ml) and extracted with ethyl acetate (2×40 ml). The combined extracts were dried (Na$_2$SO$_4$) and concentrated in vacuo to leave a yellow oil, which was chromatographed on silica gel eluting with 3% methanol/chloroform to afford the title compound as a pale pink oil (65 mg, 78%).

$^1$H NMR (CDCl$_3$)

δ: 8.08(d,1H), 7.68(d,1H), 7.05(dd,1H), 6.77(dd, 1H), 4.33(t,2H), 4.22(d,2H), 2.94–3.10(bd,2H), 2.77(t,2H), 2.30–2.45(m,2H), 2.10–2.25(m,2H), 1.77–2.07(m,5H), 1.22–1.62(m,6H), 0.93(t,3H).

5-HT$_4$ RECEPTOR ANTAGONIST ACTIVITY

1) Guinea pig colon

Male guinea-pigs, weighing 250–400 g are used. Longitudinal muscle-myenteric plexus preparations, approximately 3 cm long, are obtained from the distal colon region. These are suspended under a 0.5 g load in isolated tissue baths containing Krebs solution bubbled with 5% CO$_2$ in O$_2$ and maintained at 37° C. In all experiments, the Krebs solution also contains methiothepin 10$^{-7}$M and granisetron 10$^{-6}$M to block effects at 5-HT$_1$, 5-HT$_2$ and 5-HT$_3$ receptors.

After construction of a simple concentration-response curve with 5-HT, using 30 s contact times and a 15 min dosing cycle, a concentration of 5-HT is selected so as to obtain a contraction of the muscle approximately 40–70% maximum (10$^{-9}$M approx). The tissue is then alternately dosed every 15 min with this concentration of 5-HT and then with an approximately equi-effective concentration of the nicotine receptor stimulant, dimethylphenylpiperazinium (DMPP). After obtaining consistent responses to both 5-HT and DMPP, increasing concentrations of a putative 5-HT$_4$ receptor antagonist are then added to the bathing solution. The effects of this compound are then determined as a percentage reduction of the contractions evoked by 5-HT or by DMPP. From this data, pIC$_{50}$ values are determined, being defined as the -log concentration of antagonist which reduces the contraction by 50%. A compound which reduces the response to 5-HT but not to DMPP is believed to act as a 5-HT$_4$ receptor antagonist.

The compounds generally had a pIC$_{50}$ of at least 7.

We claim:

1. A compound according to formula (I):

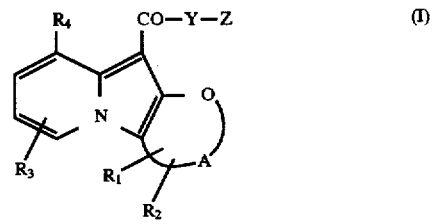

wherein:

A is a saturated polymethylene chain of 2–4 carbon atoms;

R$_1$ and R$_2$ are hydrogen, or C$_{1-6}$alkyl;

R$_3$ is hydrogen, halo, C$_{1-6}$alkyl, or C$_{1-6}$alkoxy;

R$_4$ is hydrogen, halo, C$_{1-6}$ alkyl, or C$_{1-6}$alkoxy;

Y is O or NH;

Z is of sub-formula (a), (b) or (c):

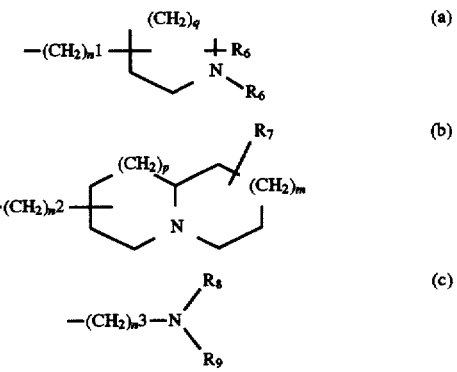

wherein n1 is 0, 1, 2, 3 or 4; n2 is 0, 1 or 2; n3 is 2, 3, 4 or 5;

q is 0, 1, 2 or 3; p is 0, 1 or 2; m is 0, 1 or 2;

R$_5$ is hydrogen, C$_{1-10}$alkyl or aralkyl;

R$_6$, R$_7$ and R$_8$ are independently hydrogen or C$_{1-6}$alkyl; and

R$_9$ is hydrogen or C$_{1-10}$alkyl;

or a pharmaceutically acceptable salt thereof.

2. A compound according to claim 1 wherein;

A is —CH$_2$—(CH$_2$)$_r$—CH$_2$—, wherein r is 0, 1 or 2;

R$_1$, R$_2$ and R$_3$ are hydrogen; and

R$_4$ is hydrogen or halo.

3. A compound according to claim 1 wherein CO-Y-Z is

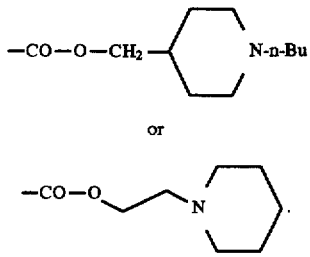

or

4. A compound according to claim 1 wherein Z is of sub-formula (a) and (CH$_2$)$_n$1 is attached at a carbon atom of the azacycle.

5. A compound according to claim 4 wherein Z is N-substituted 4-piperidylmethyl.

6. A compound according to claim 5 wherein the N-substituent is C$_2$ or greater alkyl, or optionally substituted benzyl.

7. (1-Butyl-4-piperidinyl)methyl 3,4-dihydro-2H-pyrano[2,3-b]indolizine-10-carboxylate.

8. A compound according to claim 1 but wherein Y is NH.

9. A compound according to claim 1 in the form of a pharmaceutically acceptable salt.

10. A pharmaceutical composition comprising a compound according to claim 1, and a pharmaceutically acceptable carrier.

11. A method of treating gastrointestinal disorders which comprises administering an effective amount of a compound according to claim 1.

12. A method according to claim 11 wherein the gastrointestinal disorder being treated is irritable bowel syndrome.

* * * * *